United States Patent
Lai et al.

(10) Patent No.: US 6,575,573 B2
(45) Date of Patent: Jun. 10, 2003

(54) METHOD AND APPARATUS FOR MEASURING A CORNEAL PROFILE OF AN EYE

(75) Inventors: Ming Lai, Dublin, CA (US); Jing-Gang Xie, Pleasanton, CA (US); Jay Wei, Fremont, CA (US)

(73) Assignee: Carl Zeiss Ophthalmic Systems, Inc., Dublin, CA (US)

( * ) Notice: Subject to any disclaimer, the term of this patent is extended or adjusted under 35 U.S.C. 154(b) by 93 days.

(21) Appl. No.: 09/981,054

(22) Filed: Oct. 17, 2001

(65) Prior Publication Data

US 2003/0071968 A1 Apr. 17, 2003

(51) Int. Cl.⁷ .................................................. A61B 3/10
(52) U.S. Cl. .................................... 351/212; 351/214
(58) Field of Search ................................ 351/205, 206, 351/211, 212, 214, 221, 246

(56) References Cited

U.S. PATENT DOCUMENTS

| | | | |
|---|---|---|---|
| 4,420,228 A | 12/1983 | Humphrey | 351/212 |
| 4,978,213 A | 12/1990 | El Hage | 351/212 |
| 5,307,097 A | 4/1994 | Baker | 351/212 |
| 5,404,884 A | 4/1995 | Lempert | 128/665 |
| 5,475,452 A | 12/1995 | Kuhn et al. | 351/212 |
| 5,512,965 A | 4/1996 | Snook | 351/205 |
| 5,512,966 A | 4/1996 | Snook | 351/205 |
| 5,539,837 A | 7/1996 | Lindmark | 382/100 |
| 5,592,246 A | 1/1997 | Kuhn et al. | 351/212 |
| 5,663,781 A | 9/1997 | Wilms et al. | 351/206 |
| 5,838,811 A | 11/1998 | Lindmark | 382/100 |
| 5,847,804 A | 12/1998 | Sarver et al. | 351/206 |
| 5,861,955 A | 1/1999 | Gordon | 356/360 |
| 5,870,167 A | 2/1999 | Knopp et al. | 351/212 |
| 6,099,522 A * | 8/2000 | Knopp et al. | 606/10 |
| 6,234,631 B1 | 5/2001 | Sarver et al. | 351/212 |

* cited by examiner

*Primary Examiner*—George Manuel
(74) *Attorney, Agent, or Firm*—Michael B. Einschlag

(57) ABSTRACT

Embodiments of the present invention provide a method and apparatus for measurement of a corneal profile of an eye. In particular, one embodiment of the present invention is a corneal diagnostic instrument including: (a) a Placido ring illuminator disposed to project radiation onto a cornea to generate a Placido ring image; (b) multiple slit lamp projectors disposed to project slit light beam images onto the cornea to generate slit light beam images; (c) a camera system optically disposed to detect the Placido ring image and the slit light beam images; and (d) a controller, coupled to the slit lamp projectors, the Placido ring illuminator, and the camera system, to cause the slit light beam images and the Placido ring image to be generated and detected in a predetermined sequence, wherein the controller is responsive to the detected Placido ring image and the detected slit light beam images to determine a corneal thickness profile.

27 Claims, 3 Drawing Sheets

METHOD AND APPARATUS FOR MEASURING A CORNEAL PROFILE OF AN EYE

TECHNICAL FIELD OF THE INVENTION

The present invention pertains to method and apparatus for measuring a corneal profile of an eye. In particular, the present invention relates to method and apparatus for measuring a corneal topography and a corneal thickness profile of an eye.

BACKGROUND OF THE INVENTION

Accurate measurement of a corneal topography and a corneal thickness profile is important for the safety and effectiveness of corneal refractive surgery. As is well known, the corneal topography, i.e., a curvature profile of an anterior surface of a cornea, can be provided by a corneal topographer. Further, it is also well known how to use ray-tracing algorithms to combine slit light beam images and the corneal topography to measure the corneal thickness profile.

For example, whenever a slit light beam is projected onto the cornea, and a cross section of the slit light beam on the cornea is viewed from an angle, the corneal thickness profile can be observed and analyzed. Further, if the projection angle and the viewing angle of the slit light beam are predetermined, and the corneal topography is measured, the corneal thickness profile of the cornea can be calculated from the measured width of the cross section of the intersection of the slit light beam on the cornea.

As disclosed in U.S. Pat. Nos. 5,512,965 and 5,512,966, slit light beam images are recorded by a video camera, and the recorded images are processed in a digital format to produce a corneal curvature profile (the corneal topography) and a corneal thickness profile. As disclosed, slit light beams are projected from two sides of an instrument axis, and slit light beam images are taken along the instrument axis. During the disclosed measurement procedure, the slit light beams are scanned across the cornea in a parallel direction, and a video image is taken at each step of the slit light beam scan positions. To obtain an accurate measurement of the corneal thickness profile, one needs an accurate measurement of the corneal topography with high spatial resolution. This, in turn, requires the corneal topography to be measured at a large number of points across the anterior surface of the cornea. Thus, as disclosed, a large number of slit light beam images is required to generate sufficient data to measure accurately the corneal topography and the corneal thickness profile. In practice, a commercial instrument based on the disclosed design principle takes some forty (40) images for each measurement, and as a result, the data acquisition process takes a few seconds to complete.

In light of the above, there is a need in the art for method and apparatus for measuring corneal profiles of an eye that can operate quickly.

SUMMARY OF THE INVENTION

One or more embodiments of the present invention advantageously satisfy the above-identified need in the art. Specifically, one embodiment of the present invention is a corneal diagnostic instrument that obtains a corneal topography and a corneal thickness profile. In particular, one embodiment of the present invention comprises: (a) a Placido ring illuminator disposed to project radiation onto a cornea to generate a Placido ring image; (b) multiple slit lamp projectors disposed to project slit light beams onto the cornea to generate slit light beam images; (c) a camera system optically disposed to detect the Placido ring image and the slit light beam images; and (d) a controller, coupled to the slit lamp projectors, the Placido ring illuminator, and the camera system, to cause the slit light beam images and the Placido ring image to be generated and detected in a predetermined sequence, wherein the controller is responsive to the detected Placido ring image and the detected slit light beam images to determine a corneal thickness profile.

Another embodiment of the present invention is a corneal diagnostic instrument that comprises: (a) a corneal topographer that determines a curvature profile of an anterior surface of a cornea; (b) multiple slit lamp projectors disposed to project slit light beams onto the cornea to generate slit light beam images; (c) a camera system optically disposed to detect the slit light beam images; and (d) a controller, coupled to the slit lamp projectors, the corneal topographer, and the camera system, to cause, in a predetermined sequence, (i) the slit light beam images to be generated and detected, and (ii) the corneal topographer to obtain data used to determine the curvature profile, wherein the controller is responsive to the detected slit light beam images and the curvature profile to determine a corneal thickness profile.

DETAILED DESCRIPTION

Figure 1:
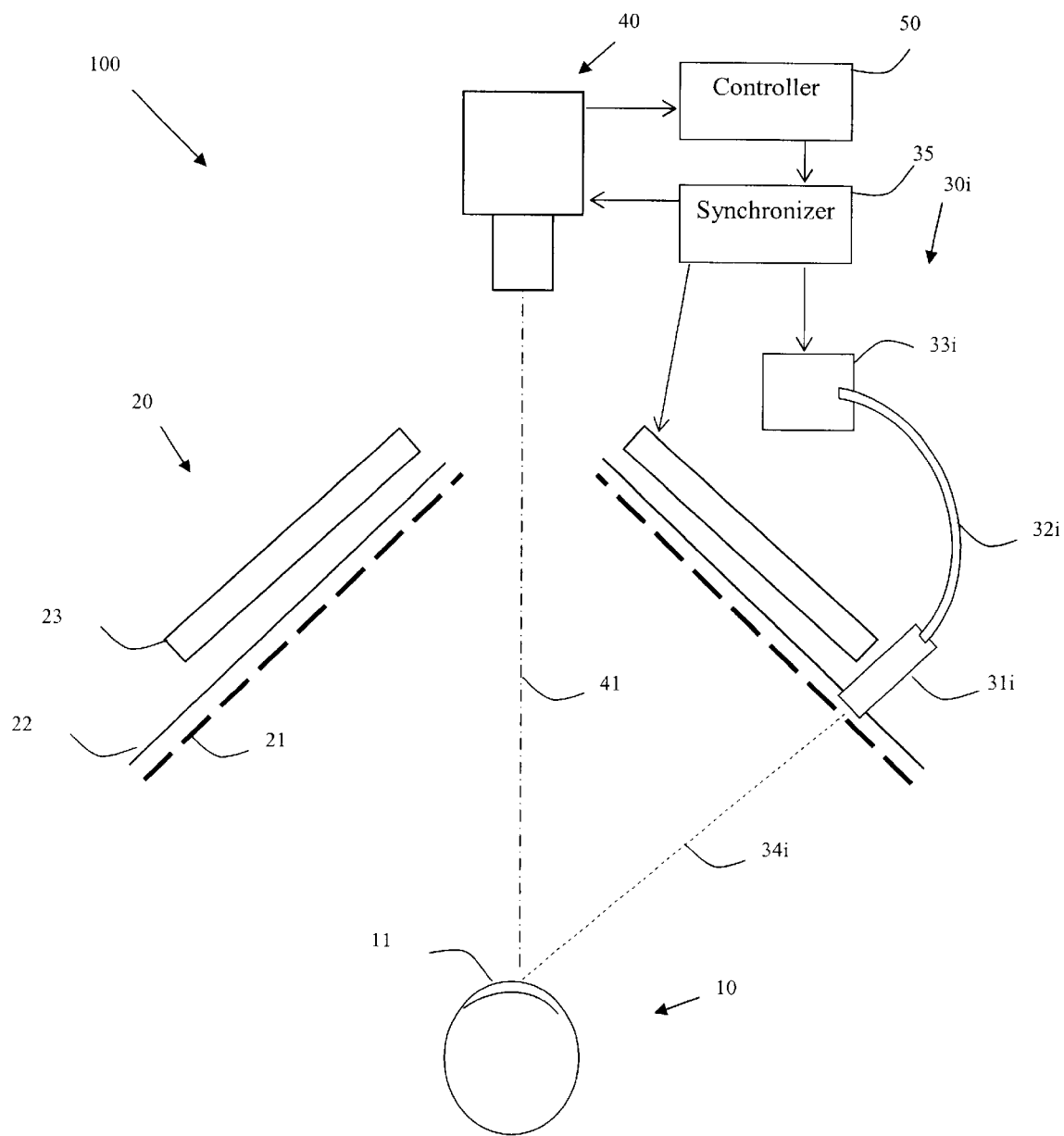
FIG. 1 is a schematic diagram of a corneal diagnostic instrument that is fabricated in accordance with one embodiment of the present invention.

FIG. 1 is a schematic diagram of corneal diagnostic instrument 100 that is fabricated in accordance with one embodiment of the present invention. As shown in FIG. 1, corneal diagnostic instrument 100 includes Placido ring illuminator 20, camera system 40, a slit lamp projector assembly, synchronizer 35, and controller 50. In accordance with this embodiment of the present invention, the slit lamp projector assembly comprises a number of slit lamp projector sub-assemblies, but only slit lamp projector sub-assembly 30i is shown in FIG. 1 to make the embodiment more readily understandable, and not to obscure further details thereof.

In accordance with this embodiment of the present invention, radiation output from Placido ring illuminator 20 is reflected by cornea 11 of subject eye 10 to form a Placido ring image that is detected by camera system 40. In one such embodiment shown in FIG. 1, Placido ring illuminator 20 comprises face plate 21 that is masked with Placido rings, diffuser plate 22, and illumination source 23. Face plate 21 determines a number and size of Placido rings in the Placido ring image, and diffuser plate 22 homogenizes radiation output from illumination source 23. Illumination source 23 can be operated to output radiation, for example and without limitation, in the visible or in the near infrared spectrum. Although visible light is more commonly used, near infrared radiation may be more favorable as it is less disturbing to subject eye 10. Face plate 21, diffuser plate 22, and illumination source 23 may be fabricated in accordance with any one of a number of methods that are well known to those of ordinary skill in the art.

The Placido ring image generated by use of Placido ring illuminator 20 is detected by camera system 40, and the detected Placido ring image output from camera system 40 is analyzed by controller 50 in accordance with any one of a number of methods that are well known to those of ordinary skill in the art to produce a corneal curvature profile of an anterior surface (i.e., a corneal topography) of cornea 11. In one embodiment, controller 50 is embodied as a computer, for example, a personal computer. Lastly, as shown in FIG. 1, synchronizer 35 applies a signal to Placido ring illuminator 20, for example, to illumination source 23, to cause it to output radiation that generates the Placido ring image at a predetermined time. Synchronizer 35 may be fabricated in accordance with any one of a number of methods that are well known to those of ordinary skill in the art. In the embodiment shown in FIG. 1, synchronizer 35 receives a signal from controller 50 that causes synchronizer 35 to generate the appropriate signal it sends to illuminator 23 of Placido ring generator 20. Additionally, synchronizer 35 sends a signal to camera system 40 to cause it to operate to detect the Placido ring image generated by radiation output from Placido ring illuminator 20 which was reflected by cornea 11. It should be understood that although synchronizer 35 may be embodied as being separate from controller 50, further embodiments of the present invention exist wherein synchronizer 35 may form a portion of controller 50.

In accordance with one embodiment of the present invention, Placido ring illuminator 20 is turned on for generating the Placido ring image, and it may be turned on for eye alignment. When it is turned on, Placido ring illuminator 20 illuminates eye 10, and a Placido ring image is reflected by cornea 11 and is imaged on camera system 40. As shown in FIG. 1, camera system 40 is positioned to view cornea 11 along instrument axis 41. Instrument axis 41 is aligned with a visual axis of eye 10 in accordance with any one of a number of methods and mechanisms that are well known to those of ordinary skill in the art (such mechanisms are not shown for clarity and ease of understanding the principles of the present invention). Although camera system 40 is shown to be physically disposed along instrument axis 41, it should be appreciated that camera system 40 may be aligned at other positions. In that case, optical systems which are well known to those of ordinary skill in the art (for example and without limitation, beam splitting systems) may be used to ensure that camera system 40 records images as if it were disposed as shown in FIG. 1, i.e., in such a case it may be said to be optically disposed along instrument axis 41.

Figure 2:
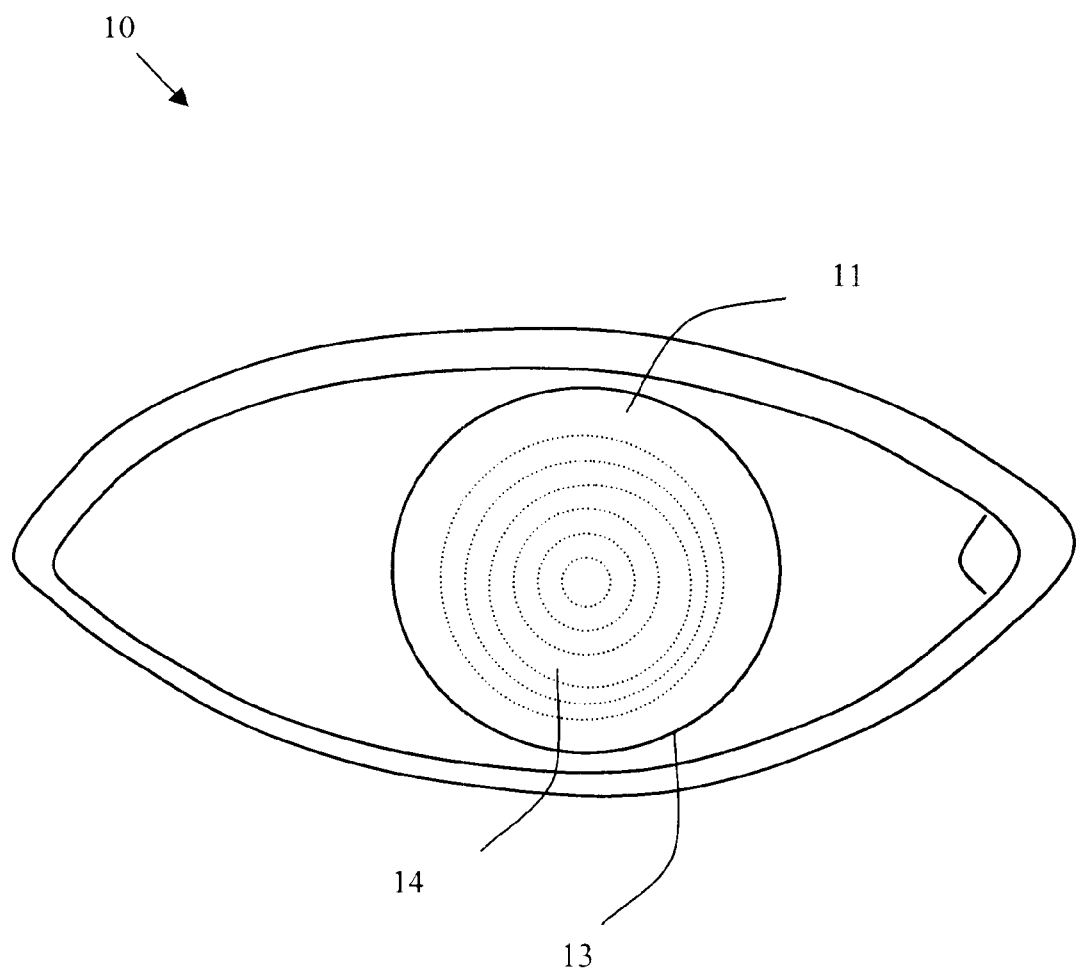
FIG. 2 is a pictorial representation of a Placido ring image obtained using the corneal diagnostic instrument shown in FIG. 1.

As is well known, the shape and size of each Placido ring carries position and curvature information of cornea 11 at the corresponding position. The Placido ring image generated by use of Placido ring illuminator 20 is detected by camera system 40, and is analyzed by controller 50 in accordance with any one of a number of methods that are well known to those of ordinary skill in the art to produce a corneal curvature profile of an anterior surface of cornea 11. FIG. 2 is a pictorial representation of Placido ring image 14 obtained using corneal diagnostic instrument 100. In particular, FIG. 2 shows how Placido ring image 14 appears relative to other landmarks of eye 10. For example, the Placido rings are typically: (a) centered with a vertex of cornea 11; and (b) in alignment with, and located within, limbus 13 of eye 10. For a perfectly spherical corneal surface, all the Placido rings in Placido ring image 14 will be concentric circles. However, whenever cornea 11 deviates from a perfectly spherical surface, the Placido rings will bend and curve, depending on the local elevation and curvature of cornea 11.

As shown in FIG. 1, slit lamp projector sub-assembly 30$i$ comprises radiation source 33$i$, optical fiber 32$i$, and slit light projector 31$i$. Optical fiber 32$i$ delivers radiation output from radiation source 33$i$ to slit lamp projector 31$i$. Although slit light projector sub-assembly 30$i$ is shown to comprise optical fiber 32$i$, further embodiments of the present invention are not so configured, and can be fabricated without using an optical fiber to deliver radiation output from radiation source 33$i$ to slit light projector 31$i$.

In accordance with one embodiment of the present invention, each slit lamp projector 31$i$ includes a slit and imaging optics that images the slit onto cornea 11. Slit light beam 34$i$ output from slit light projector 31$i$ has a typical width of about 50 to about 100 microns and a typical length about 8 to about 10 mm on cornea 11. In one such embodiment, the slit width is about 10 microns and its length is about 2 mm, and slit light beam 34$i$ has a width of about 50 microns and a length of about 10 mm on cornea 11. Many methods are well known to those of ordinary skill in the art for fabricating the slit and the image optics of slit light projector sub-assemblies 30$i$.

Radiation source 33$i$ can comprise a flash lamp or a CW lamp. In one embodiment of the present invention, each radiation source 33$i$ comprises a flash lamp that is synchronized with camera system 40 (in response to signals from synchronizer 35) for emission of radiation and for capture of images at predetermined times, respectively. In another embodiment of the present invention, radiation source 33$i$ comprises a CW lamp and an optical shutter (not shown). In such an embodiment, the optical shutter is synchronized with camera system 40 (in response to signals from synchronizer 35) for passing radiation at a predetermined time for a predetermined time period and for capture of images at predetermined times, respectively. In the embodiment shown in FIG. 1, synchronizer 35 receives a signal from controller 50 that causes synchronizer 35 to generate the appropriate signal it sends to each radiation source 33$i$ and camera system 40. It should be understood that although synchronizer 35 may be embodied as being separate from controller 50, further embodiments of the present invention exist wherein synchronizer 35 may form a portion of controller 50.

For the embodiment shown in FIG. 1, optical fiber 32$i$ can be a large core, plastic fiber. In one such embodiment, the core size of optical fiber 32$i$ is 2 mm. In accordance with the embodiment of the present invention shown in FIG. 1, use of optical fiber 32$i$ enables slit-light projector 31$i$ to be separated from radiation source 33$i$. This is advantageous because it is easy to install and align slit light projector 31$i$, and to replace a lamp included in radiation source 33$i$.

In accordance with one embodiment of the present invention, slit light projectors 31$i$ are installed around a circle in a plane that intersects face plate 21 and that is substantially perpendicular to instrument axis 41. However, the present invention is not thusly limited, and includes embodiments wherein the slit light projectors are not all in a plane or in a circle in a plane. In accordance with one such embodiment, slit light projectors 31$i$ are installed such that each slit-light beam 34$i$ has substantially the same projection angle on cornea 11, i.e., the same intersection angle with respect to instrument axis 41. In one such embodiment, each slit light beam 34i is aligned such that it intersects instrument axis 41 at approximately 45 degrees, and such that it intersects cornea 11 substantially at its center. However, the present invention is not thusly limited, and includes embodiments wherein the projection angles of at some or all of the slight light beams are different.

In one embodiment of the present invention, the number of slit light beams 34i is 4 to 8, which number of slit light beams 34i can produce sufficient data and spatial resolution to produce an accurate corneal thickness profile. In such an embodiment, an angular spacing between slit-light beams 34i is uniform on a corneal plane, for example, a 45 degree angular spacing for an embodiment having 4 slit light beams 34i and a 22.5 degree angular spacing for an embodiment having 8 slit light beams, the angular spacing being referred to as clocking angles. This is understood as follows. Each slit light beam intersects the cornea is appears as an image across the cornea. Therefore, four (4) slit light beams divide the cornea into 8 sections, and each section occupies a clocking angle of 45 degrees.

The spectrum of slit-light beams 34i can be almost any wavelength, but is preferably in the visible or near infrared. Although scattering from corneal tissue is stronger for shorter wavelengths, ultra-violet is less favorable due to its potential for causing damage to the eye. White light is commonly used in slit lamp examinations, and provides an acceptable choice for use in fabricating embodiments of the present invention. Near infrared radiation also provides an acceptable good choice, and it is less disturbing to subject eye 10 than white light.

In accordance with one embodiment of the present invention, camera system 40 is a CCD camera, and in another embodiment, camera system 40 is a video camera. In practice, the Placido ring image produced by use of Placido ring illuminator 20 and the slit light beam images produced by use of the slit lamp projector assembly are located on slightly different planes. To obtain the best quality images, one may use a camera system that comprises one camera to record the Placido ring image, and another camera to record the slit light beam images. For example, to do this, camera system 40 may further comprise a beam splitter (it can be installed in front of camera system 40 as shown in FIG. 1) to introduce a beam path for a second camera. Alternatively, one can adjust the focal plane of camera system 40 between times of obtaining the Placido ring image and the slit light beam images. To do this, camera system 40 may include a movable lens (it can be installed in front of camera system 40 as shown in FIG. 1) to adjust the image plane in a predetermined manner. Many methods are well known to those of ordinary skill in the art for fabricating a moving a lens. In some such embodiment, the lens may be moved by a linear motor in response to signals from controller 50.

When a camera system comprised of two cameras is used, the spectrum of the illumination beam used to generate the Placido ring image can be chosen to be different from the spectrum of the illumination beams used to generate the slit light beam images. Thus, the image beam path for a first camera can be separated from that for a second camera by a dichromatic beam splitter. In this way, the Placido ring image can be captured at substantially the same time as any one of the slit light beam images is captured. In addition, in a further embodiment, the spectra of the illumination beams used to generate the slit images can be chosen so that the spectra are different from one another, or the spectra of predetermined ones are different from other predetermined ones. Then, images having different spectra can be captured in different cameras of a camera system wherein the image beam paths for the different cameras are separated using beam splitters and filters in accordance with any one of a number of methods that are well known to those of ordinary skill in the art. Lastly, the image beams having different spectra can be detected at the same time.

Figure 3A:
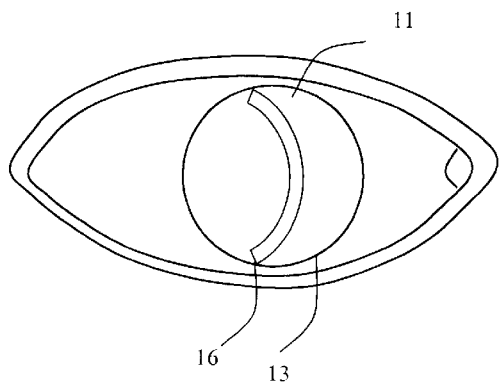
FIGS. 3a–3d are pictorial representations of four (4) slit light beam images obtained utilizing slit light beams projected from different clocking angles onto a cornea of an eye in accordance with one embodiment of the present invention.
Figure 3B:
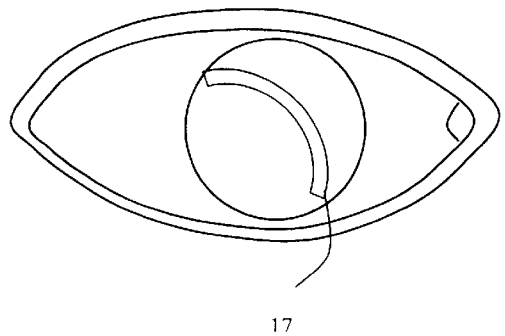
Figure 3C:
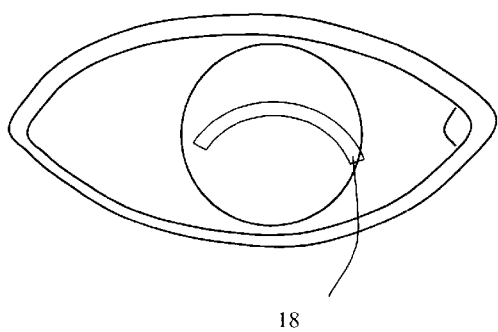
Figure 3D:
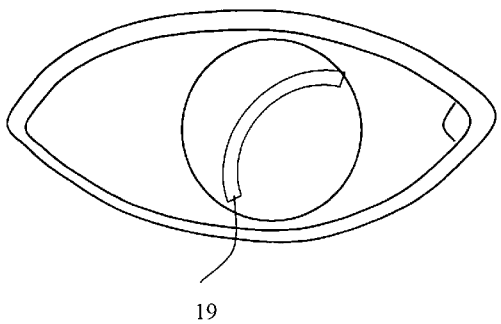

FIGS. 3a–3d are pictorial representations of four (4) slit light beam images obtained utilizing slit light beams projected from different clocking angles onto cornea 11. FIG. 3a shows slit light beam image 16 (at a viewing angle approximately along an axis of eye 10) that is formed when a slit light beam intersects eye 10 approximately at a center of cornea 11. To form slit light beam image 16 of FIG. 3a, the slit light beam is projected: (a) from a position to the right of eye 10; and (b) towards eye 10 at a predetermined angle (for example, an angle of approximately 45 degrees) with respect to the visual axis of eye 10. As is well known, a width of slit light beam image 16 is proportional to a corneal thickness, provided the width of the slit light beam is known, and provided that the width is much thinner than the corneal thickness. To calculate the corneal thickness from slit light beam image 16, the viewing angle at which the image was taken, and the projection angle of the slit light beam are predetermined. Also a local curvature of cornea 11 at every image point along slit light image 16 must be determined to enable ray tracing, through refraction, on an anterior surface of cornea 11. The principles involved in, and algorithms for using, ray tracing to determine corneal thickness are well known to those of ordinary skill in the art. For example, one can refer to U.S. Pat. Nos. 5,512,965 and 5,512,966. Similarly, FIGS. 3b–3d show slit light beam images 17–19, respectively, (at a viewing angle approximately along an axis of eye 10) that are formed when slit light beams intersect eye 10 approximately at the center of cornea 11. To form slit light beam image 17 of FIG. 3b, the slit light beam is projected: (a) from a position to the right and above eye 10; and (b) towards eye 10 at a predetermined angle (for example, an angle of approximately 45 degrees) with respect to the axis of eye 10. To form slit light beam image 18 of FIG. 3c, the slit light beam is projected: (a) from a position above eye 10; and (b) towards eye 10 at an angle of approximately 45 degrees with respect to the axis of eye 10. To form slit light beam image 19 of FIG. 3d, the slit light beam is projected: (a) from a position to the left and above eye 10; and (b) towards eye 10 at a predetermined angle (for example, an angle of approximately 45 degrees) with respect to the axis of eye 10.

In operation, in accordance with one embodiment of the present invention, Placido ring illuminator 20 and each slit lamp projector sub-assembly 30i, for example, slit light projectors 31i thereof, are turned on, one at a time in a predetermined sequence, which predetermined sequence is synchronized with camera system 40, to generate a Placido ring image and a plurality of slit light beam images. These slit light beam images can then be used by controller 50, in combination with the corneal curvature profile of the anterior surface of cornea 11 generated by analyzing the Placido ring image, to generate a corneal thickness profile. An algorithm for use in generating the corneal thickness profile may be based on triangular ray tracing, and a number of such algorithms are well known to those of ordinary skill in the art.

Advantageously, in accordance with one or more embodiments of the present invention, when corneal diagnostic instrument 100 comprises Placido ring illuminator 20 (as shown in FIG. 1), this can significantly reduce the data acquisition time when compared with the data acquisition time for designs disclosed in U.S. Pat. Nos. 5,512,965 and 5,512,966. This is because, for example, use of Placido ring illuminator 20 can generate a great deal of data points at high spatial resolution in a single image. This is advantageous for the additional reason that, since all the data points for measuring the corneal curvature profile are recorded in a single image, eye movement plays no effect on the precision of the measurement.

Further, in practice, the required number of data points and the required spatial resolution of the corneal curvature profile of the corneal anterior surface are much greater than that required to measure a corneal thickness profile. Thus, once a precise corneal curvature profile is obtained, an accurate measurement of the corneal thickness profile (along one cross section) can be obtained regardless of the number of slit light beam images used.

An additional advantage of this invention is the use of multiple slit light projectors to eliminate mechanical movement of a scanning slit light beam, and thus to further reduce data acquisition time and to minimize position error due to mechanical movement.

Those skilled in the art will recognize that the foregoing description has been presented for the sake of illustration and description only. As such, it is not intended to be exhaustive or to limit the invention to the precise form disclosed. For example, although FIG. 1 shows an embodiment wherein the Placido ring image and the slit light beam images are obtained using the same camera and are analyzed in the same controller, further embodiments of the present invention exist wherein the Placido ring image and the slit light beam images are captured in separate cameras, and are analyzed in separate controllers. For example, in one such embodiment, the corneal diagnostic instrument would comprise a corneal topographer that generates a corneal topography. In addition, in some embodiments, the predetermined sequence may include generating and detecting the Placido ring image before generating and detecting the slit light beam images, or vice versa, or some other sequence. Note that the term sequence is not restricted to a meaning of one thing after another, but is used in a more general sense. That is, the term sequence can include events where things happen at the same time, or where some things happen at the same time and others things happen one after another.

What is claimed is:

1. A corneal diagnostic instrument that comprises:
   a Placido ring illuminator disposed to project radiation onto a cornea to generate a Placido ring image;
   multiple slit lamp projectors disposed to project slit light beams onto the cornea to generate slit light beam images;
   a camera system optically disposed to detect the Placido ring image and the slit light beam images; and
   a controller, coupled to the slit lamp projectors, the Placido ring illuminator, and the camera system, to cause the slit light beam images and the Placido ring image to be generated and detected in a predetermined sequence, wherein the controller is responsive to the detected Placido ring image and the detected slit light beam images to determine a corneal thickness profile.

2. The corneal diagnostic instrument of claim 1 wherein at least one of the multiple slit lamp projectors comprises a flash lamp.

3. The corneal diagnostic instrument of claim 1 wherein at least one of the multiple slit lamp projectors comprises an optical fiber.

4. The corneal diagnostic instrument of claim 1 wherein at least one of the multiple slit lamp projectors comprises a CW light source.

5. The corneal diagnostic instrument of claim 1 wherein each of the multiple slit lamp projectors project a slit light beam at a substantially a predetermined constant angle with respect to a predetermined axis.

6. The corneal diagnostic instrument of claim 1 wherein each of the multiple slit lamp projectors projects a slit light beam with a uniform clocking angle separation from each other.

7. The corneal diagnostic instrument of claim 1 wherein at least one of the multiple slit lamp projectors projects a slit light beam having a white light spectrum.

8. The corneal diagnostic instrument of claim 1 wherein at least one of the multiple slit lamp projectors projects a slit light beam having an infrared spectrum.

9. The corneal diagnostic instrument of claim 1 wherein the multiple slit lamp projectors comprise 4 to 8 projectors.

10. The corneal diagnostic instrument of claim 1 wherein the controller comprises a synchronizer that causes the slit light beam images and the Placido ring image to be generated and detected in a predetermined sequence.

11. The corneal diagnostic instrument of claim 1 wherein the predetermined sequence causes the Placido ring image to be generated and detected before the slit light beam images are generated and detected.

12. The corneal diagnostic instrument of claim 1 wherein the predetermined sequence causes the Placido ring image to be generated and detected after the slit light beam images are generated and detected.

13. The corneal diagnostic instrument of claim 1 wherein:
   the Placido ring image comprises radiation having first wavelengths and the slit light beam images comprise radiation having second wavelengths, wherein the first and second wavelengths are different; and
   the camera system comprises a first camera that detects radiation having the first wavelengths and a second camera that detects radiation having the second wavelengths.

14. The corneal diagnostic instrument of claim 13 wherein:
   the controller provides the predetermined sequence wherein the Placido ring image is generated and detected in the first camera during at least a portion of time that the slit light beam images are generated and detected in the second camera.

15. The corneal diagnostic instrument of claim 1 wherein the camera system comprises a movable lens.

16. A corneal diagnostic instrument that comprises:
   a corneal topographer that determines a curvature profile of an anterior surface of a cornea;
   multiple slit lamp projectors disposed to project slit light beams onto the cornea to generate slit light beam images;
   a camera system optically disposed to detect the slit light beam images; and
   a controller, coupled to the slit lamp projectors, the corneal topographer, and the camera system, to cause, in a predetermined sequence, (a) the slit light beam images to be generated and detected, and (b) the corneal topographer to obtain data used to determine the curvature profile, wherein the controller is responsive to the detected slit light beam images and the curvature profile to determine a corneal thickness profile.

17. The corneal diagnostic instrument of claim 16 wherein the corneal topographer generates a Placido ring image.

18. A method for corneal diagnosis that comprises steps of:
   in a predetermined sequence, projecting radiation and multiple slit light beams onto a cornea to generate a Placido ring image and slit light beam images and detecting the Placido ring image and the slit light beam images; and
   analyzing the Placido ring image and the slit light beam images to determine a corneal thickness profile.

19. The method of claim 18 wherein the step of projecting multiple slit light beams includes generating the slit light beams utilizing at least one flash lamp.

20. The method of claim 18 wherein the step of projecting multiple slit light beams includes generating the slit light beams utilizing at least one optical fiber.

21. The method of claim 18 wherein the step of projecting multiple slit light beams includes generating the slit light beams utilizing at least one CW light source.

22. The method of claim 18 wherein the step of projecting multiple slit light beams includes projecting the slit light beams at a substantially a predetermined constant angle with respect to a predetermined axis.

23. The method of claim 18 wherein the step of projecting multiple slit light beams includes projecting the slit light beams with a uniform clocking angle separation one another.

24. The method of claim 18 wherein the step of projecting multiple slit light beams includes projecting at least one slit light beam having a white light spectrum.

25. The method of claim 18 wherein the step of projecting multiple slit light beams includes projecting at least one slit light beam having an infrared light spectrum.

26. The method of claim 18 wherein the step of projecting multiple slit light beams includes projecting 4 to 8 slit light beams.

27. A method for corneal diagnosis that comprise steps of:
   utilizing a corneal topographer to obtain a curvature profile of an anterior surface of a cornea;
   in a predetermined sequence, projecting multiple slit light beams from multiple projectors onto the cornea to generate slit light beam images and detecting the slit light beam images; and
   analyzing the curvature profile and the slit light beam images to determine a corneal thickness profile.

* * * * *